(12) United States Patent
Cheng

(10) Patent No.: US 10,849,708 B2
(45) Date of Patent: Dec. 1, 2020

(54) DEVICES AND METHODS FOR TREATING MEDICAL CONDITIONS ASSOCIATED WITH SACROILIAC JOINT ABNORMALITIES

(71) Applicant: THE CLEVELAND CLINIC FOUNDATION, Cleveland, OH (US)

(72) Inventor: Jianguo Cheng, Solon, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 772 days.

(21) Appl. No.: 14/564,309

(22) Filed: Dec. 9, 2014

(65) Prior Publication Data

US 2015/0164519 A1  Jun. 18, 2015

Related U.S. Application Data

(60) Provisional application No. 61/915,159, filed on Dec. 12, 2013.

(51) Int. Cl.
| | | |
|---|---|---|
| *A61B 90/11* | (2016.01) | |
| *A61B 18/00* | (2006.01) | |
| *A61B 17/34* | (2006.01) | |
| *A61B 18/14* | (2006.01) | |
| *A61B 90/00* | (2016.01) | |

(52) U.S. Cl.
CPC .......... *A61B 90/11* (2016.02); *A61B 18/1477* (2013.01); *A61B 2017/3411* (2013.01); *A61B 2018/00339* (2013.01); *A61B 2018/00434* (2013.01); *A61B 2018/00565* (2013.01); *A61B 2090/3966* (2016.02)

(58) Field of Classification Search
CPC ..... A61B 17/17; A61B 17/1703; A61B 17/70; A61B 17/7059; A61B 17/7076; A61B 17/88; A61B 17/8897; A61B 17/80; A61B 17/8066
See application file for complete search history.

(56) References Cited

U.S. PATENT DOCUMENTS

| | | | | |
|---|---|---|---|---|
| 4,860,331 A * | 8/1989 | Williams | ................. | A61B 6/08 116/278 |
| 6,269,148 B1 * | 7/2001 | Jessop | .................... | G01N 23/04 378/162 |
| 2008/0039866 A1 * | 2/2008 | Stetz | ...................... | A61B 90/39 606/129 |
| 2008/0140130 A1 * | 6/2008 | Chan | .................. | A61B 17/1728 606/280 |
| 2012/0296428 A1 * | 11/2012 | Donner | ............... | A61F 2/30988 623/17.11 |

* cited by examiner

*Primary Examiner* — Christopher J Beccia
(74) *Attorney, Agent, or Firm* — Tarolli, Sundheim, Covell & Tummino LLP

(57) ABSTRACT

Device and methods for treating conditions caused by or associated with a sacroiliac joint abnormality using radiofrequency ablation. A surgical jig is provided that facilitates safe, easy, and quick placement of electrodes in a patient's spinal region for radiofrequency ablation of a set of spinal nerves and/or sacroiliac ligaments.

20 Claims, 3 Drawing Sheets

DEVICES AND METHODS FOR TREATING MEDICAL CONDITIONS ASSOCIATED WITH SACROILIAC JOINT ABNORMALITIES

CROSS-REFERENCE TO RELATED APPLICATIONS

The present application claim priority to U.S. Provisional Application No. 61/915,159, filed on 12 Dec. 2013, which is incorporated by reference in its entirety.

TECHNICAL FIELD

The present invention generally relates to devices and methods for treating conditions caused by or associated with a sacroiliac joint abnormality using radiofrequency ablation.

BACKGROUND

The sacroiliac (SI) joint is the largest axial joint in the body and a complex ligamentous network supports the joint anteriorly and posteriorly. (See Anita Gupta, "Radiofrequency Ablation Techniques for Chronic Sacroiliac Joint Pain," *Pain Medicine News*; pgs. 1-7 (June 2010)). The primary function of this ligamentous system is to provide stability while allowing an adequate range of motion in multiple planes of movement. The SI joint is supported by muscles that generate stabilizing forces across the pelvic bones. These muscles include the gluteus maximus, piriformis, and biceps femoris. (See id.). These muscles' connection to the SI joint ligaments enables effective joint mobility. In approximately 30% of SI joints, there exists a potential for shearing that contributes to the acute angulation of the short horizontal articulating component. (See id.).

The lateral branches of the S1-S3 dorsal rami primarily innervate the posterior SI joint in humans with contributions from the L5 dorsal ramus in most individuals. There is reported afferent input from the S4 dorsal ramus to the long posterior sacroiliac ligament in more than 50% of SI joints. (See id.).

Pain generated in the SI joint or surrounding structures can present as low back pain, leg pain, sacral pain, pelvic pain, and/or gluteal pain. (See id.). Radiofrequency (RF) ablation has emerged as a promising treatment alternative for refractory cases of SI joint pain. Since lateral branch RF ablation was first described in the early 2000s, numerous studies have reported positive results although these studies are characterized by wide variations in technique and standards of success. (See id.).

There exists a need for a precise and straightforward system and method of using radiofrequency ablation to treat conditions caused by or associated with SI joint abnormality.

SUMMARY

Devices and methods of the present invention facilitate safe, easy, and quick placement of electrodes in a patient's spinal region for radiofrequency ablation of a set of spinal nerves for treating conditions caused by or associated with sacroiliac joint abnormality.

An embodiment of the present invention is a surgical jig device comprising a substantially rectangular body having a superior end portion and an inferior end portion. The body has a superior radiopaque marker located at the superior end portion and an inferior radiopaque marker located at the inferior end portion. The body further includes a plurality of substantially linearly aligned through-holes located between the superior and inferior radiopaque markers. Preferably, one end of each through-hole has a funnel-shaped opening to facilitate easy insertion of electrode needles as described in more detail below.

Another embodiment of the present invention provides a method of treating a medical condition of a patient suffering therefrom. The method can include identifying a patient suffering from a medical condition such as a sacroiliac joint abnormality. The method comprises obtaining a surgical jig device as described above. The method further comprises placing the jig on the patient's skin. The superior radiopaque marker is aligned with a superior anatomical location of the patient's sacrum and the inferior radiopaque marker is aligned with an inferior anatomical location of the patient's sacrum. The method further includes marking the patient's skin to indicate the position of the jig. Such marking is used to determine where to subsequently place the jig if and when the jig is removed. The method further includes inserting electrodes through the through-holes of the jig and performing therapy on the patient's spinal region to treat the patient's medical condition.

DETAILED DESCRIPTION

Figure 1:
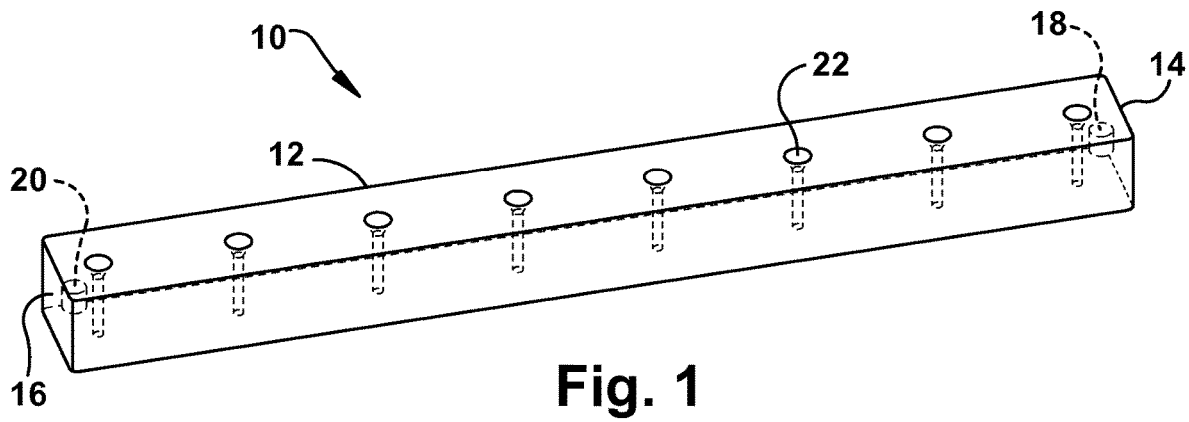
FIG. 1 is a perspective view of an embodiment of a surgical jig device of the present invention.

The disclosure herein refers to "treating" certain medical conditions. This does not necessarily mean curing the medical condition but includes improving or minimizing the patient's symptoms. The disclosure herein also refers to the term "substantially" with respect to certain geometric shapes, configurations and orientations. By "substantially" is meant that the shape, configuration or orientation of the element or feature need not have the mathematically exact described shape, configuration or orientation but can have a shape, configuration or orientation that is recognizable by one skilled in the art as generally or approximately having the described shape, configuration, or orientation. As is understood in the art, the term "surgical" device as used herein is a sterile medical device used for therapeutic purposes on a patient. A "patient" is a mammal and preferably is a human being suffering from an undesirable medical condition. The terms "lateral," "anterior" and "posterior" are used herein with respect to the anatomical directions and planes of a human body in a standard anatomical position as is known in the art. Further, as used herein with respect to a described element, the terms "a," "an," and "the" include at least one or more of the described element unless otherwise indicated. Further, the term "or" refers to "and/or" unless otherwise indicated. In addition, it will be understood that when an element is referred to as being "on," "attached" to, "connected" to, "coupled" with, "contacting," etc., another element, it can be directly on, attached to, connected to, coupled with, or contacting the other element or intervening elements may also be present. In contrast, when an element is referred to as being, for example, "directly on," "directly attached" to, "directly connected" to, "directly "coupled" with, or "directly contacting" another element, there are no intervening elements present. It will also be appreciated by those of skill in the art that references to an element that is disposed "adjacent" another element may have portions that overlap or underlie the adjacent element.

The present invention generally relates to using a surgical jig during radiofrequency ablation of target nerves in a patient's spinal region to treat medical conditions associated with sacroiliac joint abnormality. Exemplary devices and methods allow a practitioner to precisely place electrode needles in the patient's spinal region. Such devices and methods also facilitate placement of multiple needle electrodes substantially parallel to each other at desired predetermined locations (i.e. predetermined distances between electrodes). This allows a practitioner to make controlled lesions via bipolar radiofrequency to ablate target nerves to relieve medical conditions associated with sacroiliac joint abnormality. In addition to accuracy, embodiments of devices and methods allow a practitioner to place needle electrodes more easily in the patient's spinal region thereby reducing the operating time. Such operating time may be reduced by at least 50% in certain circumstances. Further, the patient's overall exposure to x-radiation can be greatly reduced compared to other methods of radiofrequency ablation to treat conditions associated with sacroiliac joint abnormalities.

Figure 2:
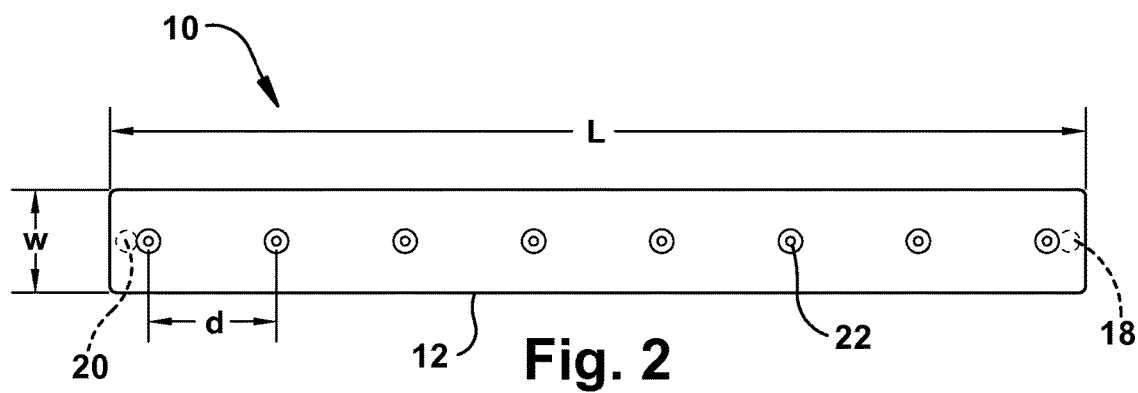
FIG. 2 is a top view of the surgical jig device of FIG. 1.
Figure 3:
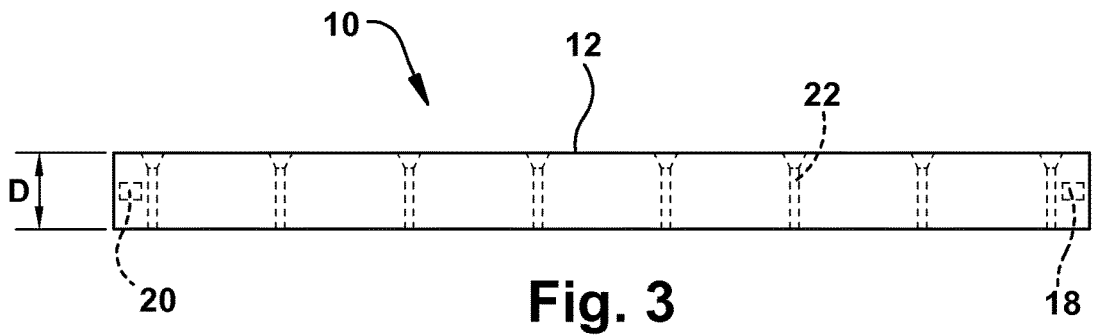
FIG. 3 is a side view of the surgical jig device of FIG. 1.

Referring to FIG. 1, in an embodiment, a surgical jig device 10 comprises a substantially rectangular body 12 having a superior end portion 14 and an inferior end portion 16. Body 12 preferably includes two radiopaque markers: a superior radiopaque marker 18 located at the superior end portion 14 and an inferior radiopaque marker 20 located at the inferior end portion 16. Body 12 also defines a plurality of substantially linearly aligned through-holes 22 located between the superior and inferior radiopaque markers 18 and 20. Preferably, as depicted in FIGS. 1 and 3, one end of each through-hole has a substantially funnel shaped opening to facilitate easy insertion of the electrodes as described below. In certain embodiments, the superior and inferior radiopaque markers are the only markers of body 12. In other embodiments, there are additional markers. As seen in FIG. 1-3, the plurality of through-holes 22 is aligned with superior and inferior radiopaque markers 18 and 20. Referring to FIG. 2, body 12 can have a length L between about 75 to about 80 millimeters and is preferably 76 millimeters long. Body 12 can have a width W between about 6 and about 10 millimeters, and is preferably 8 millimeters long. Referring to FIG. 3, body 12 can have a depth D between about 4 and about 8 millimeters and is preferably 6 millimeters deep. The plurality of through-holes can be between 5 and 10 and is preferably 8. The distance d between adjacent through-holes is preferably between about 8 and about 12 millimeters and is preferably 10 millimeters. Preferably, the through-holes are substantially equidistantly spaced.

Figure 4:
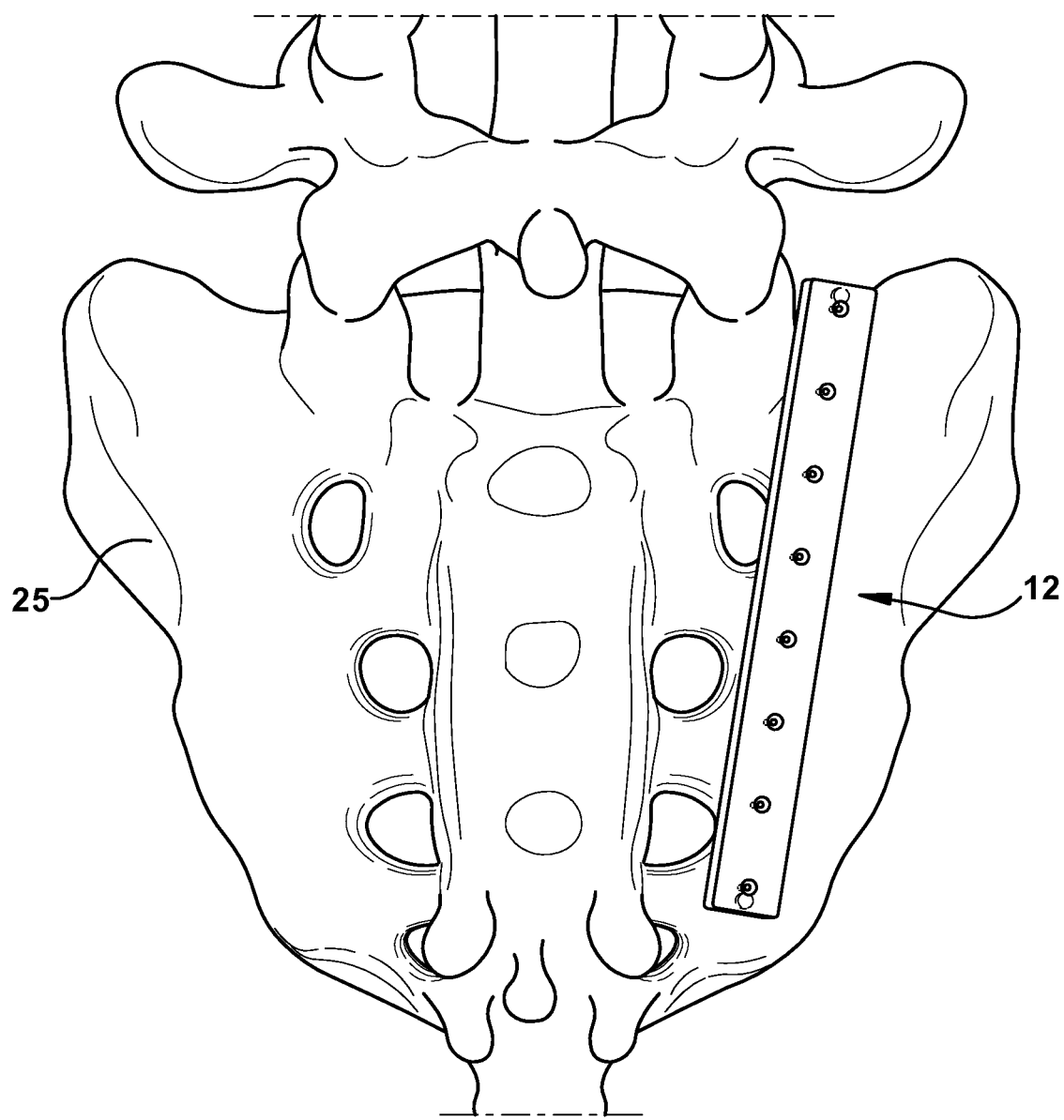
FIG. 4 is a schematic illustration of a patient's sacrum with the surgical jig of FIG. 1 placed on the patient's sacrum.
Figure 5:
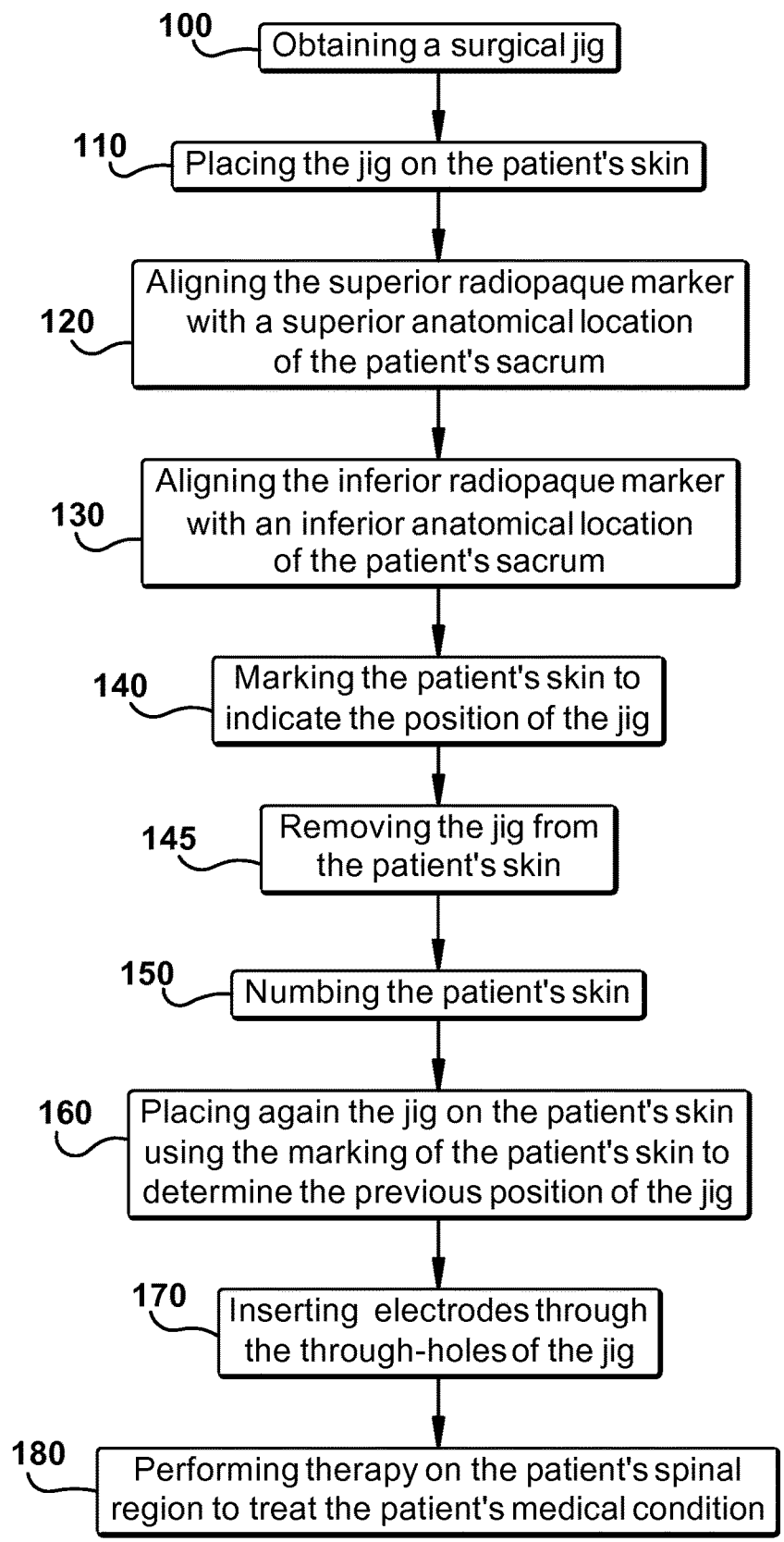
FIG. 5 is a flow chart depicting exemplary steps of a method of the present invention.

Referring to FIG. 5, an exemplary method of treating a patient suffering from a medical condition comprises obtaining a surgical jig device comprising a substantially rectangular body having a superior end portion and an inferior end portion (100). A superior radiopaque marker is located at the superior end portion and an inferior radiopaque marker is located at the inferior end portion. The body further includes a plurality of substantially linearly aligned through-holes located between the superior and inferior radiopaque markers. The method includes placing the jig on the patient's skin (110) and aligning the superior radiopaque marker with a superior anatomical location of the patient's sacrum (120) and aligning the inferior radiopaque marker with an inferior anatomical location of the patient's sacrum (130). The aligning steps are preferably performed under fluoroscopy. The method further includes marking the patient's skin to indicate the position of the jig (140). For example, a practitioner can mark the patient's skin with an "I" or other notation immediately above and below the jig using a pen or other marking device. Such marking is used to determine where to subsequently place the jig if and when the jig is removed. For example, the jig then can be removed from the patient's skin (145). The patient's skin then can be numbed (150) with local anesthetics and the jig can be placed again on the patient's skin using the marking of the patient's skin to determine the previous position of the jig (160). FIG. 4 is a schematic illustration of a jig 12 placed on a patient's sacrum 25. Electrodes, such as needle electrodes, are inserted through the through-holes of the jig (170). The through-holes are preferably sized such that there is minimal space for the needles to move laterally. The needles thereby effectively act as a fixation mechanism to maintain the position of the jig. Therapy is then performed on the patient's spinal region to treat the patient's medical condition (180). The same process can be conducted on the other side of the patient's sacrum (i.e. a bilateral procedure can be performed).

In certain embodiments, the superior anatomical location is the sacral ala. In certain embodiments, the inferior anatomical location is the lateral border of the S3 foramen of the patient's spinal region. Preferably, the lateral border is about 2 millimeters lateral of the S3 foramen.

The needle electrodes can be inserted into the patient's spinal region without necessarily using fluoroscopy and the depth of needle insertion can be controlled by the tactile indication of the needle touching bone. As such, the patient's overall exposure to x-radiation can be greatly reduced (up to 95%, for example) compared to other methods of radiofrequency ablation to treat conditions associated with sacroiliac joint abnormalities. In particular, the electrodes are preferably inserted through the through-holes of the jig to reach the posterior surface of the sacrum along a straight line starting from the sacral ala and ending at the lateral border of the S4 foramen. The electrodes are preferably aligned along this line at substantially equal distances between two adjacent electrodes and the electrodes are parallel to each other. This configuration of the electrodes can ensure the most effective bipolar radiofrequency lesions that encompass the L5 dorsal ramus and the lateral branches of the S1, S2, S3, and S4 sacral dorsal rami. This new method of radiofrequency ablation can be used to effectively and reliably denervate the posterior aspect of the sacroiliac joint for the purpose of pain relief and functional improvement.

In certain embodiments, the spinal nerve(s) that are ablated are an L5 dorsal ramus and the lateral branches of the sacral dorsal rami, such as, for example, the S1-S4 dorsal rami. In additional or alternative embodiments, a sub-branch of the lateral branch of the L4 dorsal ramus of the spinal nerve innervating the upper portion of the sacroiliac joint may be ablated.

Regarding the parameters of the electrostimulation, the radiofrequency ablation is preferably conducted by a set of parameters that determine the temperature (approximately 80-90 degrees), time (approximately 120 to 180 seconds), and cycles (approximately 1-2) of the ablation. In addition, the size (diameter) of the needle electrodes (approximately 18-22 gauge), the length of the uninsulated tip (approximately 5-15 mm) of the electrodes, and the configuration of the electrodes (straight vs. curved) can also be factors in the treatment. Bipolar radiofrequency ablation is the preferred method using this device. However, the device can also be used for other modalities of radiofrequency ablation such as cooled-probe ablation and traditional thermal ablation. In addition to spinal nerves, the radiofrequency ablation can be performed on sacroiliac ligaments or joint capsules.

Embodiments of systems and methods of the present invention can be used to treat patients suffering from conditions presented by an abnormality in the SI joint or surrounding structures, such as, for example, the surrounding ligaments and nerves. Non-limiting examples of such conditions include back pain, such as chronic low back pain; leg pain including pain that radiates down the leg on the affected side and pain in the back of the thigh; sacral pain; pelvic pain; gluteal pain; groin pain; hip pain; and/or stiffness of the lower spine. Such conditions can be due to a variety of causes including, for example, sacroiliitis, sacroiliac joint dysfunction, sacroiliac joint arthritis, sacroiliac joint disease, and/or sacroiliac joint pain.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A surgical jig device comprising:
    a substantially rectangular body having a superior end portion and an inferior end portion;
    a superior radiopaque marker located at the superior end portion;
    an inferior radiopaque marker located at the inferior end portion;
    a plurality of substantially linearly aligned through-holes located between the superior and inferior radiopaque markers, wherein the through-holes are sized to receive electrodes, the electrodes configured to fixate the surgical jig in position and apply energy treatment to a patient's spine, the jig securable to the patient's spine without an adhesive; and
    wherein the superior radiopaque marker is alignable with a superior anatomical location of the patient's spine and the inferior radiopaque marker is alignable with an inferior anatomical location of the patient's spine.

2. The surgical jig device of claim 1, wherein the inferior and superior radiopaque markers are the only radiopaque markers of the rectangular body.

3. The surgical jig device of claim 1, wherein the plurality of through-holes is substantially aligned with the inferior and superior radiopaque markers.

4. The surgical jig device of claim 1, wherein the rectangular body has a length of between about 75 and about 80 millimeters.

5. The surgical jig device of claim 1, wherein the rectangular body has a width of between about 5 and about 7 millimeters.

6. The surgical jig device of claim 1, wherein the rectangular body has a depth of between about 7 and 9 millimeters.

7. The surgical jig device of claim 1, wherein the plurality of through-holes is between about 5 and about 10 through-holes.

8. A method of treating a medical condition of a patient suffering therefrom comprising:
    placing a surgical jig device on the patient's skin, the jig comprising:
        a substantially rectangular body having a superior end portion and an inferior end portion;
        a superior radiopaque marker located at the superior end portion;
        an inferior radiopaque marker located at the inferior end portion; and
        a plurality of substantially linearly aligned through-holes located between the superior and inferior radiopaque markers;
    aligning the superior radiopaque marker with a superior anatomical location of the patient's sacrum;
    aligning the inferior radiopaque marker with an inferior anatomical location of the patient's sacrum;
    marking the patient's skin to indicate the position of the jig;
    using the marking to determine where to subsequently place the jig if and when the jig is removed;
    placing again the jig on the patient's skin using the marking of the patient's skin to determine the previous position of the jig;
    inserting electrodes through the through-holes of the jig; and
    performing therapy on the patient's spinal region to treat the patient's medical condition.

9. The method of claim 8, wherein the inferior anatomical location is the lateral border of the S3 foramen of the patient's spine, and the lateral border is about 2 millimeters lateral of the S3 foramen.

10. The method of claim 9, further comprising removing the jig from the patient's skin after marking the patient's skin to indicate the position of the jig.

11. The method of claim 10, further comprising numbing the patient's skin after removing the jig from the patient's skin.

12. The method of claim 8, wherein the medical condition is low back pain, leg pain, sacral pain, pelvic pain, gluteal pain, groin pain, hip pain, and/or stiffness of the lower spine.

13. The surgical jig device of claim 1, wherein one end of each through-hole is substantially funnel shaped.

14. The surgical jig device of claim 1, wherein the through-holes are substantially equidistantly spaced from one another.

15. A method of treating a medical condition of a patient suffering therefrom comprising:
    placing a surgical jig device on the patient's skin, the jig comprising:
        a substantially elongate body having a superior end portion and an inferior end portion;
        a superior radiopaque marker located at the superior end portion;
        an inferior radiopaque marker located at the inferior end portion; and
        a plurality of substantially linearly aligned through-holes located between the superior and inferior radiopaque markers;
    aligning the superior radiopaque marker with a superior anatomical location of the patient's sacrum;

aligning the inferior radiopaque marker with an inferior anatomical location of the patient's sacrum;

inserting one or more electrodes through the through-holes of the jig; and performing therapy on the patient's spinal region to treat the patient's medical condition.

16. The method of claim 15, further comprising marking the patient's skin to indicate the position of the jig.

17. The method of claim 16, further comprising again placing the jig on the patient's skin using the marking of the patient's skin to determine the previous position of the jig.

18. The method of claim 15, wherein the jig device is placed on the patient's skin without the use of an adhesive.

19. The method of claim 15, wherein the superior anatomical location is the sacral ala.

20. The method of claim 15, wherein the inferior anatomical location is the lateral border of the S3 foramen of the patient's spine.

* * * * *